United States Patent [19]

Gutierrez et al.

[11] Patent Number: 4,760,170

[45] Date of Patent: Jul. 26, 1988

[54] SOLUTION PROCESS FOR PREPARING METAL SALT ESTERS OF HYDROCARBYL SUBSTITUTED SUCCINIC ACID OR ANHYDRIDE AND ALKANOLS

[75] Inventors: Antonio Gutierrez, Mercerville; Jack Ryer, East Brunswick; John G. Hedin, Bridgewater; Robert A. Kleist, Bayonne; Stanley J. Brois, Westfield, all of N.J.

[73] Assignee: Exxon Research & Engineering Co., Florham Park, N.J.

[21] Appl. No.: 750,174

[22] Filed: Jul. 1, 1985

[51] Int. Cl.$^4$ .............................................. C07C 69/34
[52] U.S. Cl. .................................... 560/190; 560/195; 560/196; 556/62; 556/114; 556/133; 556/147
[58] Field of Search ............... 560/195, 196, 199, 190; 556/62, 114, 133, 147

[56] References Cited

U.S. PATENT DOCUMENTS

| 2,540,570 | 2/1951 | Cyphers | 252/46.6 |
|---|---|---|---|
| 2,561,232 | 7/1951 | Rudel et al. | 260/485 |
| 2,969,324 | 1/1961 | Knapp, Jr. et al. | 252/32.7 |
| 3,045,042 | 7/1962 | Staker | 260/485 |
| 3,048,623 | 8/1962 | Matuszak et al. | 560/195 |
| 3,117,091 | 1/1964 | Staker | 252/56 |
| 3,198,737 | 8/1965 | Calhoun | 252/48.6 |
| 3,278,566 | 10/1966 | Calhoun | 260/400 |
| 3,381,022 | 4/1968 | LeSuer | 260/404.8 |
| 3,556,997 | 1/1971 | Leinter | 252/48.6 |
| 3,576,847 | 4/1971 | Troussler et al. | 260/486 |
| 3,632,510 | 1/1972 | LeSuer | 556/147 |
| 3,634,476 | 1/1972 | Rinse | 556/114 |
| 3,717,672 | 2/1973 | McGee | 560/199 |
| 3,933,659 | 1/1976 | Lyle et al. | 252/32.7 E |
| 3,974,081 | 8/1976 | Rutkowski et al. | 252/79 |
| 4,105,571 | 8/1978 | Shaub et al. | 252/32.7 E |
| 4,176,074 | 11/1979 | Coupland et al. | 252/32.7 E |
| 4,344,853 | 8/1982 | Gutierrez et al. | 252/48.6 |

OTHER PUBLICATIONS

*Hackh's Chemical Dictionary*, (1969), McGraw-Hill, Publ., at p. 230.

*Primary Examiner*—Paul J. Killos
*Attorney, Agent, or Firm*—R. A. Maggio; M. B. Kapustij

[57] ABSTRACT

A solution process is disclosed for preparing a solubilized metal salt ester by reacting an ester compound, such as 2,2'-thiodiethyl-bis (octadecenyl) succinate ester, with a metal carboxylate, such as calcium acetate, in the process of a mixture of (a) a first co-solvent and/or third co-solvent, such as toluene and/or dodecylbenzene respectively, and (b) a second co-solvent such as methanol, to form the metal salt ester product and an effluent mixture of an acid, such as acetic acid, optional co-solvent first, and second co-solvent, followed by the optional addition of a third co-solvent, and vacuum distilling the resulting mixture to remove the effluent mixture to produce a solution of the product and third co-solvent.

16 Claims, No Drawings

SOLUTION PROCESS FOR PREPARING METAL SALT ESTERS OF HYDROCARBYL SUBSTITUTED SUCCINIC ACID OR ANHYDRIDE AND ALKANOLS

BACKGROUND OF THE INVENTION

The present invention relates to processes for preparing certain multi-functional metal salt derivatives of heteroatom containing esters, suitable for use in, inter-alia, automatic transmission fluids (ATF).

The metal salt esters which are prepared in accordance with the process of the present invention are derived from esters of hydrocarbyl substituted succinic acid or anhydride and alkanols such as thio alkanols. These materials, as well as various metal salts (e.g., Ni and Zn) thereof are described in U.S. Pat. No. 4,344,853 and British Patent Specification No. 2,085,918. The alkaline earth metal ester salt compounds are described in copending U.S. patent application Ser. No. 763,294, filed Aug. 7, 1985.

The method disclosed in these patents or application for preparing the metal salt ester involves the reaction of the free ester with a metal carboxylate or metal hydroxide in the presence of a suitable solvent such as methanol, water, or tetrahydrofuran. The metal salt ester which is formed precipitates from the reaction mixture and the precipitate is typically collected and washed several times.

A process which involves one or more washing steps is expensive to conduct. Consequently, there has been a continuing search for other processes for preparing such metal salt esters which results in a solubilized product which can be added directly to the formulation into which it is being employed, e.g., without a washing step.

The present invention was developed in response to this search.

The development of alternative processes for synthesizing such solubilized metal salt esters has been complicated by the tendency of these products to gel uncontrollably from solution producing a material essentially unsuitable for the purpose for which it is intended, namely, an additive to power transmitting fluids.

It is this problem of gel formation which the present invention overcomes.

While applicants are not aware of any patents which disclose the presently claimed process, the following patents are mentioned for background purposes.

U.S. Pat. No. 3,933,659 discloses fatty acid esters and amides as friction modifiers for functional fluids; U.S. Pat. No. 4,176,074 describes molybdenum complexes of polyisobutenyl succinic anhydride-amino alkanols as friction modifiers; U.S. Pat. No. 4,105,571 discloses glycerol esters of dimerized fatty acids as friction modifiers in lubricating oils.

Diesters of monohydrohydric alcohols, including those with sulfur linkages, which have been esterified with $C_3$-$C_{24}$ alkenyl succinic acid are disclosed in U.S. Pat. No. 2,561,232. The diesters disclosed therein are said to be useful as synthetic lubricant fluids. U.S. Pat. Nos. 3,198,737 and 3,278,566 disclose fatty esters having utility as extreme pressure agents. U.S. Pat. No. 2,540,570 discloses glycol esters of rosin or other fatty acids with thioglycols, the compounds being useful as extreme pressure additives.

U.S. Pat. Nos. 3,045,042 and 3,117,091 both disclose partial esters of alkenyl succinic anhydride with a variety of polyhydric alcohols such as 2,2'-thiodiethanol as rust preventive additives in petroleum fractions such as gasoline and other fuels. U.S. Pat. Nos. 3,576,847 and 3,556,997 disclose sulfinyl-containing alkenyl succinates useful as dispersants, corrosion inhibitors and anti-wear agents in lubricating oil and fuel compositions. U.S. Pat. No. 3,381,022 generally discloses esters of $C_{50}$ and higher hydrocarbon succinic acids suitable as additives in oils and fuels as well as being suitable plasticizers, detergents and emulsifiers.

SUMMARY OF THE INVENTION

The present invention provides a process for directly preparing a solution of a metal salt ester compound in the absence of gellation, which solution can be added directly to a power transmitting fluid without recovering the metal salt.

Accordingly, in one aspect of the present invention there is provided a solution process for reacting at least one metal carboxylate wherein the metal of said carboxylate is selected from the group consisting of Mg, Ca, Sr, Ba, Zn, Ni, Cu, and Mo, and at least one ester compound, which ester compound is formed by the reaction of:

(A) an alcohol represented by the structural formula:

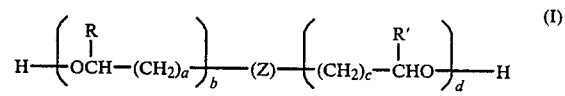

wherein R and R' each independently can represent hydrogen, or $C_1$ to $C_6$ alkyl; (a), (b), (c), and (d) each independently represent a number which can vary from 1 to about 3; and Z represents a linking group selected from —S—, —O—, and >$NR_1$, wherein $R_1$ can represent hydrogen, $C_1$ to about $C_4$ aklyl, or $C_1$ to about $C_4$ monohydroxy substituted alkyl; and (B) from about 1 to about 2 moles per mole of alcohol of an acid or anhydride represented by the respective structural formulas:

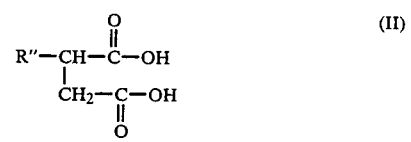

and

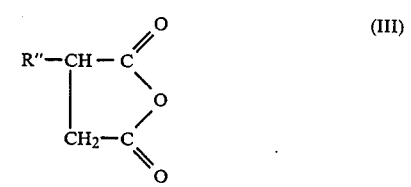

wherein R" is an aliphatic hydrocarbon group containing from about 12 to about 50 carbons, to form the corresponding metal salt of said ester compound, which comprises:

(1) admixing the ester compound and metal carboxylate with (a) at least one co-solvent selected from the group consisting of first co-solvent, third co-solvent, and mixtures thereof; and (b) at least one second co-solvent; in a manner and under conditions sufficient to (i)

avoid gel formation, (ii) dissolve said ester compound in said first co-solvent, third co-solvent or mixture thereof, and (iii) at least partially dissolve said metal carboxylate in the second co-solvent; said first co-solvent comprising at least one member selected from the group consisting of benzene, and alkyl substituted benzene having from 1 to about 3 alkyl group substituents with each alkyl group independently containing from 1 to about 5 carbon atoms; said second co-solvent being protic, and comprising at least one member selected from the group consisting of saturated aliphatic monohydric alcohol containing from about 1 to about 5 carbon atoms, phenol, $C_1$ to about $C_{15}$ alkyl substituted phenol, $C_1$ to about $C_{15}$ monohydroxy alkyl substituted benzene, water, tetrahydrofuran and mixtures thereof; said third co-solvent comprising benzene substituted with from 1 to about 3 $C_1$ to about $C_{18}$ alkyl groups, with the proviso that at least one of said alkyl groups contains from about 6 to about 18 carbon atoms, and;

(2) reacting in said admixture derived in accordance with Step (1), the metal carboxylate and ester compound at a temperature of not greater than about 100° C. in a manner and under conditions sufficient to form as a solubilized product, the corresponding metal salt of the ester compound, and an effluent mixture comprising the first co-solvent when present, second co-solvent and the corresponding acid of the metal carboxylate;

(3) admixing with the solubilized product containing admixture derived in accordance with Step (2), an amount of at least one of said third co-solvents effective to result in the dissolution of said product in the absence of said effluent mixture, when said effective amount is not present in the reacted admixture resulting upon the completion of Step (2); and (4) separating the product and third co-solvent solution from the constituents of the effluent mixture by heating the admixture derived in accordance with Step (3) at subatmospheric pressure and a temperature of not greater than about 100° C. in a manner and under conditions sufficient to evaporate said effluent mixture and remove the vapors produced thereby from the resulting solution of product and third co-solvent.

DESCRIPTION OF PREFERRED EMBODIMENTS

The esters employed in the present invention from which the metal salts thereof are prepared typically are oil soluble monoesters, diesters, and/or mixtures thereof, which esters are typically formed by the reaction of (1) an alkanol and (2) a hydrocarbon-substituted succinic acid or anhydride or mixtures thereof.

In one embodiment, the alkanol can be represented by the structural formula:

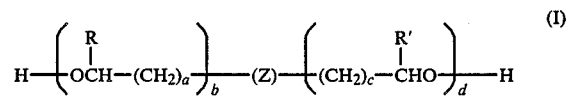
(I)

wherein R and R' each independently can represent hydrogen, alkyl (preferably straight chain alkyl), typically $C_1$ to about $C_6$ alkyl, preferably $C_1$ to about $C_3$ alkyl, and most preferably $C_1$ to about $C_2$ alkyl; (a), (b), (c), and (d) each independently represent numbers which can vary from 1 to about 3; and Z is a linking group which is selected from —S—; —O—; >$NR_1$ wherein $R_1$ can represent hydrogen, a $C_1$ to about $C_4$ alkyl group, preferably $C_1$ to about $C_3$ alkyl group, or a $C_1$ to about $C_4$ monohydroxy substituted alkyl group, preferably a terminal monohydroxy substituted alkyl group. Preferably, R and R' are the same, the numbers represented by (b) and (d) are the same as are the numbers represented by (a) and (c), thereby resulting in a bis-alkanol.

When Z is —O—, formula I can represent ethylene glycol and derivatives thereof; when Z is >$NR_1$, and $R_1$ is alcohol or hydrogen, formula I can represent a diethanol amine and derivatives thereof; when $R_1$ is a monohydroxy substituted alkyl, such as —($CH_2$)$_2$—OH, formula I can represent triethanolamine and derivatives thereof.

If b or d are greater than 1, then formula I is meant to express alkoxylated derivatives of the alkanols, such as ethoxylated derivatives. It should be further noted that when diethanolamine or its derivatives as expressed by formula I wherein $R_1$ is hydrogen are reacted with the hydrocarbyl substituted succinic acid or anhydride, the ester product mixture formed thereby can contain an ester-amide moiety, since the NH moiety of diethanolamine is available for reaction with the acid or anhydride moiety. Likewise, when $R_1$ is hydroxy substituted alkyl, the hydroxy substituent of $R_1$ is available for reaction with the acid or anhydride and the reaction product mixture can contain tris-ester moieties.

Notwithstanding the above, while reaction of the $R_1$ substituent with the acid or anhydride is possible, it is not intentionally facilitated. Consequently, the molar amounts of acid or anhydride employed to react with the alkanol are selected as though the $R_1$ substituent is inert, e.g., the acid to alcohol molar ratio will remain within the range of from about 1:1 to about 2:1 as described hereinafter in connection with mono and diesters. In such instances, mixtures of ester compounds are typically achieved.

The preferred alkanols are thio-alkanols, wherein in structural formula I, Z is —S—, and R and R' are independently hydrogen, ethyl or methyl.

The most preferred alkanols are thio-alkanols wherein in structural formula I, (a), (b), (c) and (d) are each 1 or 2, R is hydrogen or methyl, and R' is hydrogen, methyl or ethyl.

Representative alkanols include 2,2'-thiodiethanol; 3,3'-thiodipropanol; thio-bis ethoxyethanol; thio-bis isopropoxy isopropanol; oxy-bis ethanol; oxy-bis ethoxyethanol; 2,2'-diethanol methanamine; 2,2'-diethanol ethanamine; 2,2',2"-triethanolamine; 2,2'-diethanolamine; and mixtures thereof.

The hydrocarbon substituted succinic acid or anhydride which is reacted with the alkanol can be represented by the respective structural formulas:

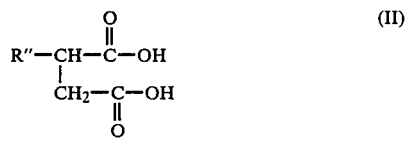
(II)

or

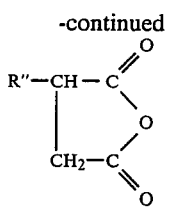

(III)

wherein R″ is an aliphatic hydrocarbon group, typically a $C_{12}$ to about $C_{50}$ aliphatic hydrocarbon group (preferably a straight chain aliphatic hydrocarbon group), preferably a $C_{16}$ to about $C_{30}$ aliphatic hydrocarbon group, and, most preferably, a $C_{18}$ to about $C_{22}$ aliphatic hydrocarbon group. The aliphatic hydrocarbon group can be alkyl, preferably straight chain alkyl, alkenyl, preferably straight chain alkenyl, isoalkyl, or isoalkenyl.

Oligomers containing the aforedescribed number of carbon atoms are also suitable as the aliphatic hydrocarbyl group, such as oligomers of $C_2$-$C_5$ monoolefins, such as isobutene.

The aliphatic hydrocarbyl group is preferably unsubstituted hydrocarbon group although it may contain substituents such as chlorine, bromine, sulfur, phosphorous, nitrogen or oxygen which will not affect the utility of the final product. A preferred substituent is sulfur as exemplified by 2-octadecylthiosuccinic anhydride.

The hydrocarbyl substituted succinic acid or anhydride compounds may be prepared by the reaction of maleic anhydride with olefins, oligomeric polyolefins, or with chlorinated derivatives thereof using techniques known in the art. Succinic acids are readily produced by hydrolysis of the corresponding anhydride. Especially preferred in preparing the ester compounds are $C_{18}$ to $C_{22}$ alkenyl succinic anhydrides, such as octadecyl succinic anhydride.

As used herein when the Z group is in fact inert, the term "monoester" or "hemiester" refers to product made from equimolar proportions of said alkanol and a succinic acid or anhydride, that is, one free hydroxyl group remains; while the term "di-ester" refers to those products using a 2:1 molar ratio of acid to alcohol wherein each hydroxyl group of the alkanol is esterified with a hydrocarbyl-substituted or polyolefin-substituted succinic acid or anhydride. In either case, at least one terminal carboxyl group of the succinic acid moiety remains, which is neutralized to form the metal salt derivative of the ester as described hereinbelow.

Formation of the mono- and di-esters employed to make the metal salt derivatives of the present invention proceeds by reacting the appropriate quantities of anhydride (or acid) and alkanol with or without an inert organic solvent diluent and heating and stirring the mixture at about 50° to 150° C. until esterification of the anhydride is complete. Equimolar quantities of each reactant will provide mainly the mono- (or hemi-) ester, and reaction of 2 moles of hydrocarbon substituted succinic acid or anhydride per mole of alkanol will provide the di-ester material. Also, products useful in the present invention encompass mixtures of such mono- and di-esters as well as mixtures of mono-esters, diesters, ester-amides, and/or tris-esters depending on the identity of the Z group when constituting $>NR_1$.

The esterification reaction time is typically controlled to be from about 10 to about 30 minutes.

Insofar as yields are concerned, the reaction of an equimolar ratio of alkanol (when Z is inert) and hydrocarbyl substituted succinic anhydride will provide a product containing about 80% mono-ester and about 20% di-ester. The di-ester is produced in somewhat higher yields, about 90% of the product being di-ester and about 10% mono-ester when the mole ratio of succinic anhydride to alkanol is 2:1.

The metal salt derivatives of the di-ester compounds of this invention are preferred embodiments exhibiting generally better thermal and oxidative stability and offering better friction modification properties.

In view of the above, a simplified structural formula of the resulting ester product derived from the succinic acid reactant and an alkanol wherein Z is inert, can be represented as follows:

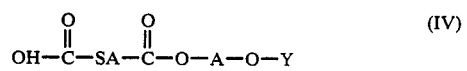

(IV)

wherein SA represents the succinic acid moiety depicted by formula II above exclusive of the terminal carboxyl groups; (A) represents the alkanol moiety depicted by formula I exclusive of the terminal hydroxyl groups; Y represents hydrogen when the product is a hemi-ester, and:

when the product is a di-ester.

The maximum carbon chain length of the R″ substituent, is affected by the propensity of increasingly longer chains to come out of solution as the fluid composition containing the same is cooled to lower and lower temperatures. The insolubilization of such substituents is undesirable because it results in agglomeration of the same as well as the formation of nucleation sites for wax crystal formation. Thus, the particular maximum substituent chain length selected will be affected by the ultimate end use for which the additive will be employed in terms of the temperature regimens to which it will be exposed.

Once a suitable ester additive has been prepared, it is converted to the metal salt thereof, said metals being selected from the alkaline earth metals including Mg, Ca, Sr, Ba; as well as Zn, Ni, Cu, and Mo, and mixtures thereof. The preferred metals are calcium and magnesium.

The metal salt esters are prepared by reacting the ester with a metal carboxylate, typically a metal carboxylate containing from about 1 to about 11, preferably from about 2 to about 6, and most preferably from about 2 to about 4 carbon atoms. Typically, the metal carboxylate can be represented by the structural formula:

wherein M is the metal, x is the valence of metal M, n is a number equal to x, and $R_2$ is a hydrocarbyl group selected from alkyl, typically about $C_1$ to about $C_{10}$ alkyl, preferably $C_1$ to about $C_6$ alkyl, and most preferably about $C_1$ to $C_3$ alkyl. In addition, the $R_2$ hydrocarbyl group can contain one or more additional carboxyl groups, typically 1 to 3 additional carboxyl groups.

The selection of an appropriate carboxylate is primarily influenced by the requirement that it, and the corresponding acid formed therefrom be at least partly soluble in at least one of the co-solvents employed, and the acid is capable of being volatilized under the separation conditions described herein. Otherwise, the carboxylate merely acts as an inert carrier for the metal which forms the metal salt ester.

Representative examples of suitable carboxylates include acetate, propanoate, butanoate, and mixtures thereof.

The preferred carboxylates are the acetate and the propanoate.

To conduct the process of the present invention, the ester and the metal carboxylate are admixed with (a) at least one first co-solvent at least one third co-solvent, or a mixture of first and third co-solvents and (b) at least one second co-solvent.

The functional characteristics of the first co-solvent include (1) at least partial, preferably complete, miscibility with the second and third co-solvents employed; (2) compatibility with, and capability of dissolving, the ester as well as the metal salt formed therefrom under the reaction conditions employed; and (3) the capability of being vaporized under the separation conditions employed to remove the same from the metal salt ester product.

First co-solvents which possess the above characteristics are liquid aromatic compounds at room temperature, containing 6 carbons in the aromatic ring (i.e., benzene), which aromatic ring can be optionally substituted with from about 1 to about 3, $C_1$ to about $C_5$, preferably $C_1$ to about $C_3$ alkyl groups.

Representative examples of suitable first co-solvents include benzene, toluene, xylene, trimethylbenzene, cumene, diethylbenzene, dibutylbenzene, and mixtures thereof.

The preferred first co-solvent is toluene.

The functional characteristics of the second co-solvent include (1) at least partial, preferably complete, miscibility with the first and third co-solvents employed; (2) the capability of dissolving at least a portion of the metal carboxylate, preferably all of the metal carboxylate; and (3) the capability of being vaporized under the separation conditions described herein. The second co-solvent helps to reduce foaming problems and to stabilize the reaction temperature. Moreover, the product is insoluble in the second co-solvent alone.

Second co-solvents which possess the above characteristics are protic, and include saturated aliphatic monohydric, alcohols containing from about 1 to about 5, preferably from bout 1 to about 3, and most preferably from about 1 to about 2 carbon atoms, phenol, and $C_1$ to about $C_{15}$, preferably $C_5$ to about $C_{12}$, most preferably $C_8$ to $C_{12}$ alkyl, preferably straight chain alkyl, substituted phenols; and monohydroxy alkyl, preferably straight chain terminal monohydroxy alkyl, substituted benzenes wherein the alkyl group thereof contains typically from about 1 to about 15, preferably from about 5 to about 12, and most preferably from about 8 to about 12 carbon atoms.

Representative examples of suitable alkanols include methanol; ethanol; propanol; isopropanol; butanol; phenol; dodecylphenols such as 4-dodecyl-1-phenol, 2-hexyl-1-phenol, 12-phenyl-1-dodecanol, 6-phenyl-1-hexanol, phenyl methanol and mixtures thereof.

Other suitable second co-solvents include water, tetrahydrofuran, and mixtures thereof.

In short, any of the above-identified second co-solvents can be employed alone or in conjunction with any one or more of the other second co-solvents.

The preferred second co-solvent is methanol.

In one embodiment of the present invention a reaction admixture (referred to herein as the initial reaction admixture) comprising first and second co-solvents, ester and metal carboxylate in prepared in which the metal salt forming reaction takes place.

In another embodiment of the present invention, the third co-solvent, hereinafter defined, may also be present in the initial reaction admixture in addition to first and second co-solvents, ester, and metal carboxylate.

In still another embodiment of the present invention, the first co-solvent may be completely eliminated and replaced by the third co-solvent in the initial reaction mixture.

However, when a first co-solvent is employed in the initial reaction admixture, it must be eventually removed as part of the effluent mixture as described hereinafter. This results from the fact that the front co-solvent is incompatible with the lubricating oil composition into which the metal salt additive is eventually introduced.

Unlike the first co-solvent, however, the third co-solvent is typically not removed, whether employed alone or in conjunction with the first co-solvent in the initial reaction admixture.

Accordingly, for purposes of the preparation of the initial reaction admixture, the first and third co-solvents are treated as performing essentially the same functions of dissolving at least a portion of the metal carboxylate. Consequently, the first and third co-solvents are treated essentially as equivalents in preparing the initial reaction admixture relative to the amounts thereof employed.

Whether additional third co-solvent must be added to the reaction admixture before removal of the effluent mixture, as described hereinafter, depends on the amount of thirid co-solvent originally present in the initial reaction mixture relative to the amount of metal salt ester product eventually produced. More specifically, the amount of such additional third co-solvent employed is dictated and controlled by the goal of having sufficient third co-solvent present upon the removal of the effluent mixture to dissolve the metal salt ester product at room temperature.

Thus, where no third co-solvent is employed in forming the initial reaction mixture, effective metal salt ester product solubilizing amounts of this co-solvent must be added prior to removal of the effluent mixture.

However, where the amount of third co-solvent employed in forming the initial reaction mixture is sufficient to dissolve not only the ester reactant (alone or in combination with first co-solvent) but also is sufficient to dissolve the metal salt ester product after removal of the effluent mixture, no additional third co-solvent need be added prior to said effluent mixture removal.

Without wishing to be bound by any particular theory, it is believed that the second co-solvent dissolves the metal carboxylate, which is otherwise substantially insoluble in the first and/or third co-solvent(s), and acts as a phase transfer agent bringing the metal carboxylate and ester into contact thereby initiating the reaction which produces the metal salt ester that remains solubilized in the first and/or third co-solvent(s). This is all achieved without gelling, provided the co-solvents and reactants are mixed in the proper sequence.

More specifically, it has been found that the metal carboxylate, must not be brought into contact with the first and/or third co-solvent(s), before it is contacted with the second co-solvent, otherwise gelling will occur.

The preferred method of mixing is to dissolve the ester in a mixture of (a) first and/or third co-solvent(s), and (b) second co-solvent, followed by the addition of the metal carboxylate to the mixture.

Alternatively, the ester can be dissolved in the first and/or third co-solvent(s) to form a first solution, and the metal carboxylate dissolved in the second co-solvent to form a second solution, and the two solutions then mixed.

In a third alternative, the metal carboxylate can be added to a mixture of (a) first and/or third co-solvent(s), and (b) second co-solvent, followed by the addition of the ester to the mixture.

The relative proportions of the ester and metal carboxylate which are admixed together are determined by stoichiometric considerations which are a function of the valence of the metal of the metal carboxylate, and the mole fraction of hemi- or di-ester components in the ester.

Thus, when using a divalent metal in the metal carboxylate and a diester, the ester and metal carboxylate are mixed at about a 1:1 mole ratio.

Likewise, about a 2:1 molar ratio of ester:metal carboxylate would be employed using a divalent metal and hemi-ester.

In short, typically each equivalent of free acid on the ester is admixed with about $X^{-1}$ moles of metal carboxylate, where X is the valence of the metal in the metal carboxylate.

The amount of first and/or third co-solvent(s) employed in the initial reaction mixture is sufficient to dissolve the ester. Thus, while any effective amount of such co-solvent(s) can be employed, it is contemplated that such effective amount typically will constitute from about 5 to about 50, preferably from about 5 to about 30, and most preferably from about 5 to about 10%, by weight, based on the weight of the ester and first and/or third co-solvent(s) present.

The amount of the second co-solvent employed in the reaction mixture is related to the amount of metal carboxylate employed, and should be effective to dissolve at least some of the metal carboxylate. Since the metal salt ester product which forms is readily soluble in the first and/or third co-solvent(s), the second co-solvent can be employed in very small amounts and still be effective.

Accordingly, while any effective amount of second co-solvent can be employed it is contemplated that such effective amount will constitute typically from about 3 to about 50, preferably from about 5 to about 20, and most preferably from about 5 to about 10%, by weight, based on the weight of second co-solvent and metal carboxylate.

Upon forming the initial reaction mixture of (a) first and/or third co-solvent(s), (b) second co-solvent(s), (c) metal carboxylate, and (d) ester, the same is heated to a temperature of not greater than about 100° C., typically not greater than about 95° C., and preferably not greater than about 90° C., which temperatures typically can range from about 65 to about 100, preferably from about 75 to about 95, and most preferably from about to about 80 to about 90° C., until the reaction is complete. Reaction times can vary from about 2 to about 6 hrs. If the reaction temperature exceeds about 100° C., a gel is formed which is undesirable. One indication of the completion of the reaction is the substantial absence of the carbonyl adsorption band in the I.R. spectrum of the reaction mixture.

The metal salt ester forming reaction is typically conducted at atmospheric pressure, although sub-atmospheric or supra-atmospheric pressures can also be employed. The metal salt ester forming reaction is typically coducted under an inert atmosphere, such as $N_2$, to avoid oxidation, although air can be employed.

The resulting reaction mixture comprises the metal salt ester product, optional third co-solvent, and an effluent mixture comprising optional first co-solvent, second co-solvent, and the corresponding acid of the metal carboxylate and any other contaminants such as water which care undesirable in the final product solution.

Third co-solvent is added, when needed as described herein, to the reaction mixture prior to removal of the effluent mixture from the product, and typically after the metal salt ester forming reaction is completed. The functional characteristics of the third co-solvent include (1) the capability of dissolving the metal salt ester product under ambient conditions; (2) at least partial, preferably complete, miscibility with at least the first co-solvent (when a first co-solvent is employed), and preferably also the second co-solvent; (3) a boiling point above the boiling points of the first and second co-solvents under separation conditions employed herein to enable separation; and (4) compatibility, with the constituents of the formulation in which the metal salt ester will eventually be employed.

Suitable third co-solvents which possess the above characteristics include $C_1$ to $C_{18}$ alkyl substituted benzenes, wherein at least one of the alkyl group(s) thereof contains from about 6 to about 18, preferably from about 10 to about 18, and most preferably from about 12 to about 18 carbons. The benzene ring can be substituted with from 1 to about 3, preferably 1, of such $C_6$ to about $C_{18}$ alkyl groups which can be straight or branched chain as well as cyclic. In addition to at least one $C_6$ to $C_{18}$ alkyl group on the alkyl substituted benzene, the remainder of the permissible alkyl substituents may contain from 1 to about 5 carbon atoms.

Representative examples of suitable third co-solvents include dodecylbenzene; octadecyl benzene; 4-isoctyl toluene and isomers thereof; 5-decyl-p-xylene and isomers thereof; 1,3-didodecyl-5-methylbenzene and isomers thereof; cycylohexylbenzene; and mixtures thereof.

The preferred thid co-solvent is dodecylbenzene.

The total amount of third co-solvent present in the reaction mixture prior to effluent removal is not critical and is sufficient to dissolve, under ambient conditions, the metal salt ester product after removal of the effluent mixture.

Accordingly, while any effective total amount of third co-solvent can be employed prior to effluent removal, it is contemplated that such effective amounts will constitute typically from about 30 to about 65, preferably from about 40 to about 60, and most preferably from about 45 to about 55%, by weight, based on the combined weight of the product, effluent mixture and third co-solvent.

Typically, when third co-solvent is added after completion of the metal salt ester forming reaction, such addition is conducted while the product and effluent mixture are still at reaction temperature as described herein.

Upon completion of the addition of any required third co-solvent, the resulting mixture is subjected to separation conditions wherein the effluent mixture is vaporized and removed from contact with the third co-solvent having the product dissolved therein.

It has been found that if the temperature at which separation is conducted exceeds about 100° C., a gel will form.

Consequently, the mixture of product, third co-solvent, and effluent are heated under conditions of temperature and pressure sufficient to permit varporization and removal of the effluent mixture from the product and third co-solvent but at a temperature below which gelling is observed.

Thus, while any effective separation conditions of temperature and pressure can be employed, it is contemplated that such effective separation temperature at which the product, third co-solvent, and effluent are heated will typically be not greater than about 100° C., preferably not greater than about 95° C., and most preferably not greater than about 90° C., and generally can range from about 65 to about 100, preferably from about 75 to about 95, and most preferably from about 80 to about 90° C.

The corresponding pressure employed in conjunction with such separation temperatures, will generally be subatmospheric, and typically range from about 10 to about 1, preferably from about 8 to about 3, and most preferably from about 5 to about 4 mm Hg.

Typically, the separation step is conducted using vacuum distillation at the effective separation temperatures disclosed above.

Upon vaporization and removal of the effluent mixture from the product and third co-solvent, the product remains dissolved in the third co-solvent. The third co-solvent thereafter acts as a solubilizing carrier for this metal salt ester product, which mixture of carrier and product can be added directly to formulations; e.g., of power transmitting fluids, without ever isolating the ester product. This results in substantial cost savings in the preparation of this product as well as the formulation into which it is added. It will be observed that at no time during the metal salt forming procedure, and thereafter, is the ester reactant or product derived therefrom, present in insolubilized form. Consequently, the present invention is referred to as a solution process.

The process of the present invention can be performed as a batch reaction, as a continuous reaction or as a semi-continuous reaction.

In the batch reaction, the reactants and co-solvents are charged, in the appropriate sequence, into a reaction vessel, and the effluent eventually removed by vacuum distillation.

In a continuous process, the reactants and first and second co-solvents can be charged into an elongated reactor, in the appropriate sequence, at a rate that substantially complete reaction will have taken place by the time the reaction mixture reaches the reactor outlet, third co-solvent added when needed, and the effluent removed. In a semi-continuous process, the reaction is conducted by metering the reaction mixture components into a series of two or more tank reactors at the appropriate rate to maintain reactor liquid level and switching from one tank to the other for effluent removal.

The metal salt of the ester prepared by the process of the present invention has been found to possess anti-oxidant, anti-corrosion, and friction modification properties, and its primary utility is as a multifunctional additive in automatic transmission fluids.

ATF systems are compounded from a number of additives each useful for improving a chemical and/or physical property of the ATF. The additives are usually sold as a concentrate package in which mineral oil is present. The mineral lubricating oil will constitute from about 40 to about 60 weight percent of the package and is a refined hydrocarbon oil or a mixture of refined hydrocarbon oils selected according to the viscosity requirements of the particular ATF but typically would have a viscosity range of 34–150, e.g., 75–150; SSU at 37.8° C. Suitable base oils include a wide variety of light hydrocarbon mineral oils, such as, naphthenic base, paraffin base, and mixtures thereof.

Additives typically present in ATF formulations include viscosity improvers, corrosion inhibitors, oxidation inhibitors, friction modifiers, dispersants, demulsifiers, antifoaming agents, anti-wear agents, pour print depressants and seal swellants.

The viscosity improvers that may be employed in ATF include any of the types known to the art including polyisobutylene, copolymers of ethylene and propylene, polymethacrylates, methacrylate copolymers, copolymers of an unsaturated dicarboxylic acid and vinyl compound and interpolymers of styrene and acrylic esters.

Corrosion inhibitors, also known as anti-corrosive agents, reduce the degradation of the metallic parts contained by the ATF. Illustrative of corrosion inhibitors are zinc dialkyldithiophosphate, phosphosulfurized hydrocarbons and the products obtained by reaction of a phosphosulfurized hydrocarbon with an alkaline earth metal oxide or hydroxide, preferably in the presence of an alkylated phenol or of an alkylphenol thioester, and also preferably in the presence of carbon dioxide. Phosphosulfurized hydrocarbons are prepared by reacting a suitable hydrocarbon such as a terpene, a heavy petroleum fraction of a $C_2$ to $C_6$ olefin polymer such as polyisobutylene, with from 5 to 30 weight percent of a sulfide of phosphorus for $\frac{1}{2}$ to 15 hours, at a temperature in the range of 150° to 600° F. Neutralization of the phosphosulfurized hydrocarbon may be effected in the manner taught in U.S. Pat. No. 2,969,324.

Oxidation inhibitors reduce the tendency of mineral oils to deteriorate in service which deterioration is evidenced by the products of oxidation such as sludge and varnish-like deposits on the metal surfaces. Such oxidation inhibitors include alkaline earth metal salts of alkylphenol thioesters having preferably $C_5$ to $C_{12}$ alkyl side chains, e.g., calcium nonylphenol sulfide, barium t-octylphenol sulfide, zinc dialkyldithiophosphates, dioctylphenylamine, phenylalphanaphthylamine, phosphosulfurized or sulfurized hydrocarbons, etc.

Dispersants maintain oil insolubles, resulting from oxidation during use, in suspension in ATF thus preventing sludge flocculation and precipitation. Suitable dispersants include high molecular weight alkylsuccinates, the reaction product of oil-soluble polyisobutylene succinic anhydride with ehtylene amines such as tetraethylene pentamine and borated salts thereof.

Pour point depressants lower the temperature at which the ATF will flow or can be poured. Such depressants are well known. Typical of those additives which usefully optimize the low temperature fluidity of the ATF are $C_8$–$C_{18}$ dialkylfumarate vinyl acetate copolymers, polymethacrylates, and wax naphthalene condensation products.

Foam control is provided by an anti-foamant of the polysiloxane type, e.g., silicone oil and polydimethyl siloxane.

Anti-wear agents as their name implies reduce wear of the transmission parts. Representative of suitable anti-wear agents are zinc dialkyldithiophosphate, zinc diaryldithiophosphate and magnesium sulfonate.

Some of these numerous additives can provide a multiplicity of effects, e.g., a dispersant-oxidation inhibitor. This approach is well known and need not be further elaborated herein.

Seal swellants which are present in combination with the friction modifier of the invention include mineral oils of the type that provoke swelling and aliphatic alcohols of 8 to 13 carbon atoms such as tridecyl alcohol with a preferred seal swellant being characterized as an oil-soluble, saturated, aliphatic or aromatic hydrocarbon ester of from 10 to 60 carbon atoms and 2 to 4 ester linkages, e.g., dihexylphthalate, as are described in U.S. Pat. No. 3,974,081.

ATF compositions contain these conventional additives and are typically blended into the mineral oil base in the following ranges thereby providing their normal attendant function.

| Components | Vol % | wt % |
|---|---|---|
| V.I. Improver | 1-15 | 1-16 |
| Corrosion Inhibitor | 0.01-1 | 0.01-1.5 |
| Oxidation Inhibitor | 0.01-1 | 0.01-1.5 |
| Dispersant | 0.5-10 | 0.5-11 |
| Pour Point Depressant | 0.01-1 | 0.01-1.5 |
| Demulsifier | 0.001-0.1 | .001-0.15 |
| Anti-Foaming Agents | 0.001-0.1 | .001-0.15 |
| Anti-Wear Agents | 0.001-1 | .001-1.5 |
| Seal Swellant | 0.1-5 | 0.1-6 |
| Friction Modifiers | 0.01-1 | 0.1-1.5 |
| Mineral Oil Base | Balance | Balance |

As a result of the multifunctional properties possessed by the metal salt ester additives of the present invention, the use of separate corrosion inhibitors, oxidation inhibitors, and friction modifiers can be eliminated in lieu of employing the additive described herein. This simplifies the final ATF composition and reduces the possibility of adverse interaction between the components employed therein.

Furthermore, because of the more stringent requirements of ATF formulations relative to friction modification, the metal salt additives of the present invention can be employed in a variety of other compositions such as hydraulic fluids, heavy duty power transmitting fluids, power steering fluids, tractor universal oils, and the like wherein strict friction modification properties are not a requirement. Such fluids are referred to herein generically as power transmitting fluids.

In a broad sense therefore, the metal salt ester is employed in a power transmitting fluid comprising a major amount of a liquid hydrocarbon of lubricating viscosity, and a minor amount of said metal salt ester effective to impart one or more of the properties of corrosion inhibition, oxidation inhibition and friction modification relative to the absence of said additive. Additional conventional additives selected to meet the particular requirements of a selected type of power transmitting fluid can be included as desired.

More specifically, while the metal salt ester additive can be employed in the above-described fluid compositions in any effective amount, it is contemplated that such effective amounts constitute typically from about 0.05 to about 2, preferably from about 0.1 to about 0.5, and most preferably from about 0.3 to about 0.6%, by weight, based on the total weight of the composition into which it is added.

When employed in an ATF formulation, such effective amounts can constitute from about 0.5 to about 2, preferably from about 0.1 to about 1, and most preferably from about 0.35 to about 0.6% (e.g., 0.5 to 0.6%), by weight, based on the weight of the ATF.

When not employing a concentrate package, the metal salt additives of the present invention, can typically be added to the appropriate power transmitting fluid as a solution of the same in the third co-solvent, said metal salt additives being present in solution in an amount of typically from about 0.1 to about 2, preferably from about 0.1 to about 1, and most preferably from about 0.1 to about 0.6%, by weight, based on the weight of the metal salt additive and third co-solvent.

The following examples are given as specific illustrations of the claimed invention. It should be understood, however, that the invention is not limited to the specific details set forth in the examples. All parts and percentages in the examples as well as in the remainder of the specification are by weight unless otherwise specified.

EXAMPLE 1

Part A

The diester of a 2-octadecenyl succinic anhydride with 2,2'-thio-bis-ethanol was prepared by adding 0.5 mole of the alcohol to a mole of the anhydride at 120° C. The reaction mixture was stirred at this temperature until the anhydride carbonyl adsorption band is absent in the IR spectrum of the reaction mixture. This compound can be represented by the formula:

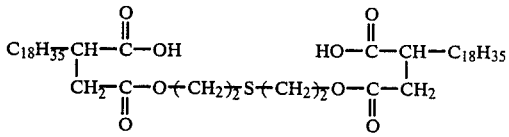

Part B

Using the diester product produced in accordance with Part A, the following run was conducted:

About 150 lbs. of 2,2'-thiodiethyl bis(octadecenyl)-succinate ester, 117.3 lbs. of toluene and 3 gallons of methanol were charged into the reactor and stirred while heating to a temperature of 65° C. to dissolve the ester. Once solution was attained, 29.6 lbs. of calcium acetate.$0.5H_2O$ was added, and the reaction mixture heated to 85° C. with a nitrogen blanket. This temeprature was maintained for 3 hours. Infrared analysis showed complete conversion to the calcium salt of the ester. Then, 157.3 lbs. of dodecylbenzene was added, and the reactor contents were vacuum distilled at a temperature of 95° C. to remove toluene, methanol, acetic acid, and water. The resulting 50% solution of metal salt ester in dodecylbenzene was filtered and the filtrate analyzed. The results of the analysis showed 1.71% sulfur, and 2.15% calcium, which reflects a 46.8% active ingredient of product in dodecylbenzene.

The resulting metal salt diester product can be represented by the following structural formula:

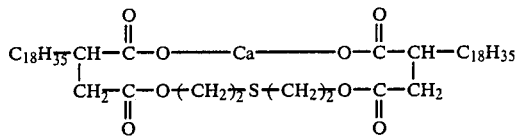

Comparative Example 1

Example 1, Part B, was repeated with the exception that the reaction temperature was increased from 85° C. to 115° C.

A substantial amount of gelling was observed.

Comparative Example 2

Example 1, Part B, was repeated with the exception that the temperature of vacuum distilliation was increased to 105° C.

A substantial amount of gelling was observed.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A solution process for reacting at least one metal carboxylate wherein the metal of said carboxylate is selected from the group consisting of Mg, Ca, Sr, Ba, Zn, Ni, Cu, and Mo, and at least one ester compound, which ester compound is formed by the reaction of:

(A) an alcohol represented by the structural formula:

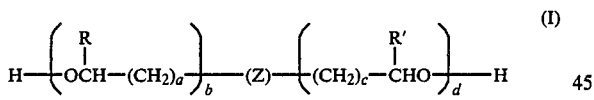

wherein R and R' each independently can represent hydrogen or $C_1$ to $C_6$ alkyl; (a), (b), (c), and (d) each independently represent a number which can vary from 1 to about 3; and Z represents a linking group selected from —S—, —O—, and $NR_1$ wherein $R_1$ can represent hydrogen, $C_1$ to about $C_4$ alkyl, or $C_1$ to about $C_4$ monohydroxy substituted alkyl; and (B) from about 1 to about 2 moles per mole of alcohol of an acid or anhydride represented by the respective structural formulas:

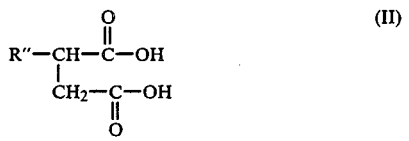

and

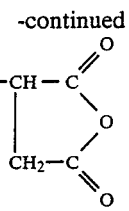

wherein R″ is an aliphatic hydrocarbon group containing from about 12 to about 50 carbons; to form a solution of the corresponding metal salt of said ester compound which comprises:

(1) admixing the ester compound and metal carboxylate with (a) at least one co-solvent selected from the group consisting of first co-solvent and third co-solvent; and (b) at least one second co-solvent; in a manner and under conditions sufficient to (i) avoid gel formation, (ii) dissolve said ester compound in said first co-solvent, third co-solvent or mixture thereof, and (iii) at least partially dissolve said metal carboxylate in the second co-solvent; said first co-solvent comprising at least one member selected from the group consisting of benzene, and alkyl substituted benzene having from 1 to about 3 alkyl group substituents with each alkyl group independently containing from 1 to about 5 carbon atoms; said second co-solvent comprising at least one member selected from the group consisting of saturated aliphatic monohydric alcohol containing from about 1 to about 5 carbon atoms, phenol, $C_1$ to about $C_{15}$ alkyl substituted phenol, $C_1$ to about $C_{15}$ monohydroxy alkyl substituted benzene, water, and tetrahydrofuran; said third co-solvent comprising benzene substituted with from 1 to about 3 $C_1$ to about $C_{18}$ alkyl groups, with the proviso that at least one of said alkyl groups contains from about 6 to about 18 carbon atoms, and;

(2) reacting in said admixture derived in accordance with Step (1) the metal carboxylate and ester compound at a temperature of not greater than about 100° C. in a manner and under conditions sufficient to form as a solubilized product, the corresponding metal salt of the ester compound, and an effluent mixture comprising the first co-solvent when present, second co-solvent and the corresponding acid of the metal carboxylate;

(3) admixing with the solubilized product containing admixture derived in accordance with Step (2) an amount of at least one of said third co-solvents effective to result in the dissolution of said product in the absence of said effluent mixture, when said effective amount is not present in the reacted admixture resulting upon the completion of Step (2); and (4) separating the product and third co-solvent solution from the constituents of the effluent mixture by heating the admixture derived in accordance with Step (3) at subatmospheric pressure and a temperature of not greater than about 100° C. in a manner and under conditions sufficient to evaporate said effluent mixture and remove the vapors produced thereby from the resulting solution of product and third co-solvent.

2. The process of claim 1 wherein the metal carboxylate is represented by the structural formula:

$(R_2-COO^-)_n M^x$ wherein M is the metal, (x) is the valence number of the metal M, n is a number equal to (x), and $R_2$ is a $C_1$ to $C_{10}$ alkyl group, the alcohol of structural formula I is a bis-alkanol wherein R and R' are the same, (a) and (c) are the same, (b) and (d) are the same; and R" of the acid or anhydride of structural formulas II and III is a $C_{12}$ to $C_{50}$ straight chain alkyl group.

3. The process of claim 1 wherein the metal carboxylate is calcium acetate, magnesium acetate or mixtures thereof; the first co-solvent is selected from the group consisting of benzene, mono-, di-, or tri-alkyl substituted benzene wherein each alkyl group contains from 1 to 3 carbon atoms; the second co-solvent is at least one $C_1$ to $C_5$ monohydric alkanol; and the third co-solvent is an alkyl substituted benzene wherein the alkyl group thereof contains from about 10 to 18 carbons.

4. The process of claim 1 wherein the reaction of Step (2) is conducted at a temperature of from about 65° to about 100° C., and the separation of the effluent mixture from the product and third co-solvent, is conducted at a temperature of from about 65° to about 100° C.

5. The process of claim 1 wherein the metal carboxylate is calcium acetate, magnesium acetate of mixtures thereof; the ester compound is the reaction product of thio-bis ethanol and octadecenyl succinic acid or anhydride; the first co-solvent is selected from the group consisting of toluene, xylene, benzene and mixtures thereof; the second co-solvent is selected from the group consisting of methanol, ethanol, propanol, butanol dodecylphenol and mixtures thereof; and the third co-solvent is selected from the group consisting of octadecyl benzene, dodecylbenzene; and mixtures thereof.

6. The process of claim 5 wherein the ester compound, a first co-solvent and a second co-solvent are admixed, followed by the addition of the metal carboxylate to the admixture.

7. The process of claim 1 wherein Step (1) is conducted in the absence of a first co-solvent and in the presence of a third co-solvent.

8. The process of claim 1 wherein Step (1) is conducted in the presence of a mixture of first and third co-solvents.

9. The process of claim 1 wherein Step (1) is conducted in the absence of a third co-solvent.

10. The process of claim 1 wherein the reaction temperature of Step (2) is from about 75° to about 95° C., and the separation tempreature of Step (4) is from about 75° to about 95° C.

11. The process of claim 1 wherein the metal carboxylate is a metal acetate, the ester compound is the reaction product of thio-bis ethanol, and a $C_{18}$ to $C_{22}$ straight chain hydrocarbyl substituted succinic acid or anhydride; the first co-solvent is selected from the group consisting of toluene, xylene, and benzene; the second co-solvent is selected from the group consisting of methanol, ethanol, and propanol; and the third co-solvent is dodecyl benzene.

12. The process of claim 11 wherein the reaction of the metal carboxylate and ester compound is conducted at a temperature of from 80° to about 90° C., and the separation Step (4) is conducted at a temperature of from 80° to about 90° C.

13. The process of claim 12 wherein the first co-solvent is toluene, the second co-solvent is methanol, the metal of the metal carboxylate is selected from the group consisting of calcium, magnesium, and mixtures thereof; and the ester compound is the reaction product of thio-bis ethanol, and octadecenyl succinic acid or anhydride.

14. The process of claim 13 wherein the ester compound is a diester.

15. The process of claim 13 wherein the ester compound is a mixture of mono- and diesters.

16. The process of claim 1 wherein Z of structural formula (I) is —S—.

* * * * *